Figure 1:
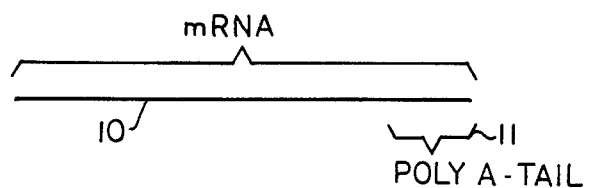

United States Patent [19]

Bahl et al.

[11] Patent Number: 4,555,486
[45] Date of Patent: Nov. 26, 1985

[54] METHOD FOR USING AN AMINO-TERMINUS DNA SEQUENCE TO SYNTHESIZE A SPECIFIC DOUBLE-STRANDED DNA

[75] Inventors: Chander P. Bahl, El Cerrito; Jack Nunberg, Oakland, both of Calif.

[73] Assignee: Cetus Corporation, Emeryville, Calif.

[21] Appl. No.: 468,805

[22] Filed: Feb. 28, 1983

Related U.S. Application Data

[63] Continuation of Ser. No. 214,119, Dec. 8, 1980, abandoned.

[51] Int. Cl.⁴ .................... C12P 21/00; C12P 21/02; C12N 15/00; C12N 1/00; C07H 21/04
[52] U.S. Cl. ......................................... 435/91; 435/68; 435/70; 435/172.3; 435/317; 536/27; 935/16; 935/17; 935/18
[58] Field of Search .................. 435/68, 70, 91, 172.3, 435/317; 536/27; 935/16, 17, 18

[56] References Cited

U.S. PATENT DOCUMENTS

4,401,759  8/1983  Rubin et al. ..................... 435/91

OTHER PUBLICATIONS

Houghton and Stewart et al.; Nucl. Acids Res. 8, 1913 (1980).
Houghton, Eaton et al.; Nucl. Acids Res. 8, 2885 (1980).
Wickens, M. P. et al., *J. Biol. Chem.*, 253:2483-2495 (1978).
Buell, G. N. et al., *J. Biol. Chem.*, 253:2471-2482 (1978).
Goodman, H. M. and MacDonald, R. J. *Methods in Enzmology*, 68:75-91 (1979).
Efstratiadis et al.; Cell 7, 279 (1976).
Chan et al.; Proc. Natl. Acad. Sci., USA 76, 5036 (1979).
Sanger et al., "DNA sequencing with chain-terminating inhibitors", Proc. Natl. Acad. Sci. USA 74: 5463 (1977).
Houghton et al., "The amino-terminal sequence of human fibroblast interferon as deduced from reverse transcripts obtained using synthetic oligonucleotide primers", Nucleic Acids Res. 8: 1913 (1980).
Houghton et al., "The complete amino acid sequence of human fibroblast interferon as deduced using synthetic oligodeoxyribonucleotide primers of reverse transcripase", Nucleic Acids Res. 8: 2885.
Efstratiadis et al., "Enzymatic in vitro synthesis of globin genes", Cell 7: 279 (1976).
Chan et al., "Construction and selection of recombinant plasmids containing full-length complementary DNAs corresponding to rat insulins I and II", Proc. Natl. Acad. Sci. USA 76: 5036 (1979).

*Primary Examiner*—Thomas G. Wiseman
*Assistant Examiner*—James Martinell
*Attorney, Agent, or Firm*—Albert P. Halluin; Elliott L. Fineman; Janet E. Hasak

[57] ABSTRACT

A method is described for constructing double-stranded DNA using messenger RNA templates. DNA strands complementary to the templates are formed using a non-specific 3' hydroxy terminus primer. After separation, the DNA single strands are disabled from self priming by blocking the free 3' hydroxy. Primer segments are then provided complementary to a portion of the amino terminus-coding end of the desired single strands. These primer segments are then extended with a suitable polymerase to complete the complementary strands.

12 Claims, 5 Drawing Figures

U.S. Patent   Nov. 26, 1985   4,555,486

METHOD FOR USING AN AMINO-TERMINUS DNA SEQUENCE TO SYNTHESIZE A SPECIFIC DOUBLE-STRANDED DNA

This application is a continuation of application Ser. No. 214,119, filed Dec. 8, 1980, abandoned.

This invention relates generally to recombinant DNA technology and, more particularly, to an improved method for constructing double-stranded DNA corresponding to a specific strand of messenger RNA.

With the advent of recombinant DNA techniques, genetic information, either synthesized or isolated from one strain or species, may be inserted into the genetic makeup of another strain or species. The strain or species into which the recombinant sequence is introduced produces, as part of its normal processes, the protein encoded by the newly introduced DNA. When the modified strain or species proceeds with the normal replication process, it also duplicates the inserted sequence.

Much of the work in the area of recombinant DNA has thus far involved strains of E. coli or some other bacteria, into the genetic system of which has been introduced desired eukaryotic genetic information. Examples include the genetic information for human growth hormone, insulin, and interferon. The successful isolation of a desired eukaryotic DNA sequence is typically a complex and involved process. Moreover, the complexity and length of many genetic units, particularly mammalian genes, may make synthesis by known techniques a prodigious or impossible task.

In some cases, in vitro techniques exist by which the amount of messenger RNA from a particular eukaryotic gene may be enriched in the total RNA. Because of this enrichment, it is advantageous to use the enriched total messenger RNA as a template for producing complementary DNA which will be correspondingly enriched. With the discovery of the enzyme RNA-directed polymerase (reverse transcriptase) (retrovirus) it became possible to produce DNA complementary to messenger RNA, selecting only the messenger RNA for transcription as opposed to other RNAs present in a mixture. Since most eukaryotic messenger RNAs contain, at their 3' hydroxy termini, regions rich in poly (A), (a region of recurring A ribonucleotides) it is possible to hydrogen bond to each of such regions a complementary segment of DNA bases (T). This segment may then serve as a primer to support the synthesis of complementary DNA on the remaining part of the messenger RNA strand, catalyzed by reverse transcriptase (J. Biol. Chem., Volume 253, Number 7, pages 2471–2482, Apr. 10, 1978).

Using this technique, double-stranded DNA complementary to eukaryotic messenger RNAs has been produced. (J. Biol. Chem., Volume 253, Number 7, pages 2483–2495, Apr. 10, 1978). Using the single DNA strand produced by use of reverse transcriptase, a complementary DNA strand is produced by the enzyme polymerase I (or polymerase II) followed by treatment with S1 nuclease to cleave unwanted DNA.

Prior art techniques for producing double-stranded DNA from messenger RNA must surmount the difficulty of selecting, out of the reaction mixture, the desired double-stranded DNA. Thus, even though the synthesized DNA is enriched for the desired sequence, a purification technique must be introduced at some point in the procedure. This can be done by purifying the messenger RNA, or it can be done by suitable labeling or other techniques to select, from the synthesized DNA, the DNA of interest. Either procedure requires the screening of many clones to identify a pure clone of interest. Such screening is often a laborious process and, in some cases, is not practical.

It is an object of the present invention to provide an improved method for producing double-stranded DNA from messenger RNA.

Another object of the invention is to provide an improved method for constructing double-stranded DNA corresponding to a specific strand of messenger RNA in a mix of a plurality of different messenger RNA strands.

Another object of the invention is to provide an improved method for constructing double-stranded DNA from messenger RNA in which selection of the desired DNA is readily achieved.

Other objects of the invention will become apparent to those skilled in the art from the following description, taken in connection with the accompanying drawings wherein FIGS. 1 through 5 illustrate, schematically, successive steps in one form of the method of the invention.

Very generally, the method of the invention, in a preferred form, constructs double-stranded DNA corresponding to a specific strand of messenger RNA in a mix of a plurality of different messenger RNA strands. Single strands of DNA are formed complementary to the messenger RNA strands in the mix using a non-specific primer. The thus formed single strands of DNA are separated from the complementary messenger RNA strands. Primer segments of DNA are then used as primers on the selected desired DNA corresponding to the specific strand of messenger RNA. These primers are formed to be complementary to the section of the desired cDNA proximate 3' ends. The primer segments are then extended with bases complementary to the single strands to which they are annealed, forming double-stranded DNA corresponding to the specific strand of messenger RNA.

Referring now to FIG. 1, the drawing depicts, schematically, a typical piece of eukaryotic messenger RNA (mRNA). Total mRNA may be isolated from the cellular material which produced the protein or peptide of interest. Naturally, in addition to the mRNA of interest, this total mRNA contains other messenger RNAs complementary to a variety of different DNAs other than the one which is of interest. Various types of enrichment techniques may provide more of the desired messenger RNA than occurs naturally.

However, typical prior art techniques for constructing double-stranded DNA corresponding to a specific strand of messenger RNA in a mixture of RNA strands require one or more manipulations such as organic extractions, ethanol precipitations, chromatography, sucrose gradient ultracentrifugation and gel electrophoresis, to select the desired DNA material. Many studies require purification on acrylamide gels or the screening of large numbers of transformant before selection of the desired DNA can be achieved. The present invention greatly simplifies the procedure for constructing double-stranded DNA from messenger RNA by providing a high selectivity.

Most naturally occurring eukaryotic messenger RNA (a strand of which is represented as 10 in FIG. 1) carries a poly A tail, represented by the portion under the bracket 11 in FIG. 1. This tail, which may consist of the order of 150 A ribonucleotide bases, may be used as a site for annealing a primer segment of DNA bases complementary to the RNA bases. Such a primer segment may be readily synthesized in accordance with known techniques, or may be obtained by other suitable means from a naturally occurring system. Such a non-specific DNA primer may, for example, consist of 12-15 T bases of DNA molecules.

Figure 2:
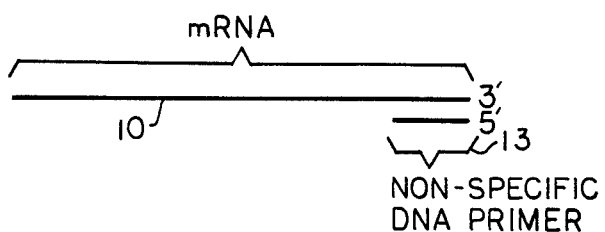

In FIG. 2, the non-specific poly A tail 11 has annealed to it the non-specific primer, indicated by the line under the bracket 13. The non-specific DNA primer is a poly T segment of DNA and will anneal, under proper conditions, to the poly A tails of the messenger RNA. It is not necessary that the primer anneal to the typically much longer tail at any particular location. As discussed below, extension of the primer with reverse transcriptase will fill in the remainder of the tail with complementary T bases.

The non-specific DNA primer is then extended using the enzyme reverse transcriptase. The enzyme results in the formation of a complementary strand of DNA ((−) strand cDNA) extending along the remaining portion of the messenger RNA strands, initiated at the non-specific DNA primer 13. The (−)strand cDNA is indicated by the portion of the line within the bracket 14.

Figure 3:
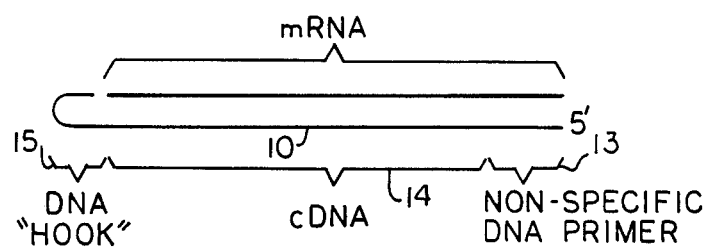
Figure 4:
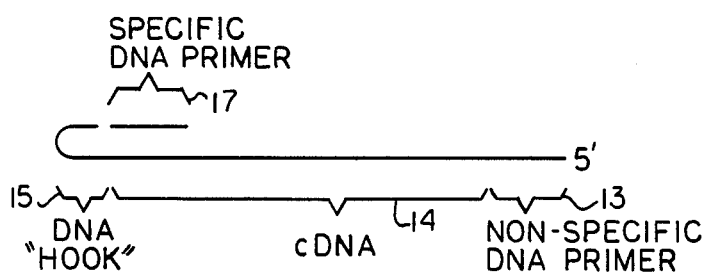

Reverse transcriptase products, whether partial or complete copies of the messenger RNA template, often possess characteristics which, it is assumed, are caused by short partially double-stranded hairpins (sometimes referred to as loops or hooks) at their 3' termini. In FIG. 3, the segment within the bracket 15 represents the DNA hook which is appended to the complementary DNA 14. These hairpins or hooks can be utilized as primers for DNA polymerases. Accordingly, one technique known in the prior art is to separate the messenger RNA strands 10 from the thus formed complementary DNA strands 14, utilizing suitable known separation techniques. For example, using an alkali treatment, (Goodman and McDonald, *Methods in Enzymology*, Vol. 68, Ed. Wu, Academic Press, N.Y., p. 75) the RNA is degraded but the DNA is left intact. This is followed by exposure to DNA polymerase whereby the hook 15 serves as a primer for the formation and extension of a complementary DNA strand, complementary to the first DNA strand 14. Accordingly, a double-strand of DNA is thus formed. The loops or hooks may be cleaved with the single strand specific nuclease, S1, to generate duplex DNA suitable for insertion into a bacterial plasmid. This is possible because the loop or hook has sufficient single stranded character as to be susceptible to the S1 nuclease.

A problem with this prior art technique is that all of the DNA hooks, both on the strands of interest and on all of the other strands of DNA formed by the reverse transcriptase, will prime the extension of complementary DNA segments. Accordingly, a further selection is necessary in order to retrieve the desired double strands from the mix. Additionally, a further, and perhaps more significant problem with the aforementioned prior art technique is that information encoded by certain nucleotide bases is lost when the hooks are used to prime the extension of the (+) strand cDNA.

The present invention obviates the necessity for a purification or selection step at this point; the selection is inherent in the method of the invention. In accomplishing the method of the invention, the DNA hairpins or hooks are disabled from their priming or self-priming function. This is accomplished by adding to the ends of the hooks a molecule which serves as a chain terminator, having its 3' end blocked. Such may be accomplished through the use of 2'-3' dideoxynucleoside triphosphates, or cordycepin triphosphate. Such treatment prevents the attachment, in the presence of DNA polymerase, of any nucleosides which would extend the hook. When thus disabled, generation of a DNA strand complementary to the strand 14 requires the use of exogenously added primer.

In accordance with the method of the invention, a specific DNA primer, included in the bracket 17 (FIG. 4), is annealed proximate the amino terminus coding end of the (−) strand cDNA. This primer is formed as complementary to a known sequence of DNA bases in the strand 14. Such information may be obtained without the necessity of determining the complete amino acid sequence of the protein of interest, since most sequencing devices begin at the amino terminus of the protein. By synthesizing a sufficient number of bases for the specific DNA primer 17, coding for the first several amino acids of the protein, a selection pressure may be achieved to provide a desired probability of extending only those DNA segments of interest. If the specific DNA primer happens to anneal to a particular strand of DNA other than at its 5' end, selection may be easily achieved since the molecular weight will differ or since the resulting strands will contain single strand extensions.

Figure 5:
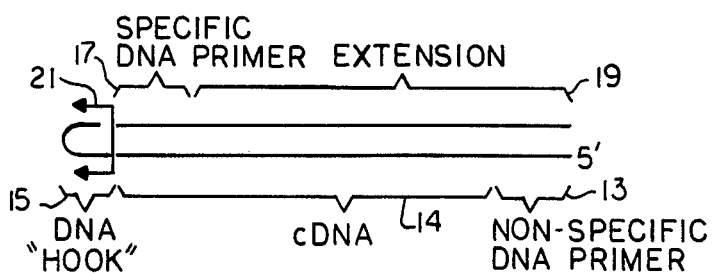

The specific DNA primer is then extended using a suitable DNA polymerase, such as DNA polymerase I. Under these conditions, bases complementary to the lower strand 14 form as an extension of the specific DNA primer 17. This completes the upper strand of DNA, indicated by the bracket 19, as shown in FIG. 5. The DNA hairpin or hook 15 may then be cleaved using the specific nuclease S1 as previously mentioned, as shown by the arrows 21. The resultant double-stranded DNA is now suitable for insertion in a bacterial plasmid.

By way of further explanation of the method of the invention, the following examples are given. However, such examples are not intended to limit the scope of the invention, which is defined by the appended claims.

EXAMPLE I—HUMAN INSULIN

In order to clone the human insulin gene, total RNA from human pancreas cellular material is isolated. Complementary DNA is then made by utilizing oligothymidylic acid as primer, all four deoxynucleoside triphosphates, and reverse transcriptase, as described by Goodman and McDonald, *Methods in Enzymology*, Academic Press New York, Ray Wu, Editor, Volume 68, 1980, page 75.

The 3' hydroxy ends of the DNAs are then blocked to prevent subsequent participation in chain elongation. This is accomplished by incubating the DNA with a solution of alpha 32 P cordycepin triphosphate in cacodylate buffer containing one mM $CoCl_2$ and deoxynucleotidyl terminal transferase. After no more cordycepin is incorporated in DNA (i.e. after completion of the reaction) the DNA is purified using standard procedures.

Alternatively, 3' blocking may be accomplished by heating the complementary DNA to 37° C. with a DNA polymerase such as Pol I or reverse transcriptase in the presence of 100–500 mM of a mixture of 4 nucleoside triphosphate (containing 1 or more nucleosides in the 2'-3' dideoxy form) in a buffer appropriate for the polymerase used. After no more triphosphates are incorporated, the DNA is purified using standard techniques.

The DNA molecules whose 3' ends are now blocked by a chain terminator are used as a template for DNA polymerase-catalyzed elongation of oligodeoxynucleotide primers. These primers are chemically synthesized based on known amino terminus sequence data. Sixteen possible DNA primers based on the first four amino acids at the end terminus (Phe-Val-Asn-Gln) are chemically synthesized with the base possibilities being as follows:

| Phe | Val | Asn | Gln |
| --- | --- | --- | --- |
| TTC | GTT | AAT | CA |
| TTT | GTC | AAC | |
| | GTG | | |
| | GTA | | |

The fragments individually or as a mixture, are used as primers for synthesizing the second strand of DNA. One of these primers will have the same sequence as the natural RNA.

EXAMPLE II—HUMAN GROWTH HORMONE

Human growth hormone may be prepared by isolating total RNA from human pituitary. Complementary DNA is then made by utilizing oligothymidylic acid as primer, all four deoxynucleaside triphosphates, and reverse transcriptase, as described by Goodman and McDonald, *Methods in Enzymology,* Academic Press New York, Ray Wu, Editor, Volume 68, 1980, page 75.

The 3' hydroxyl ends of the complementary DNA are then blocked to prevent their subsequent participation in chain elongation. This may be accomplished by either of the techniques of Example I.

After blocking the 3' hydroxy ends of the complementary DNA molecules, these molecules are now used as a template for DNA polymerase catalyzed elongation of oligodeoxynucleotide primers chemically synthesized based upon the known amino terminus sequence data. For human growth hormone, the first four amino acids at the N terminus of growth hormone are Phe-Pro-Thr-Ileu. The DNA primers chosen (32 are possible) will therefore be a combination of the following possible bases:

| Phe | Pro | Thr | Ileu |
| --- | --- | --- | --- |
| TTT | CCT | ACT | AT |
| TTC | CCA | ACC | |
| | CCG | ACG | |
| | CCC | ACA | |

The fragments, individually or as a mixture, may then be used as primers for synthesizing the second strand of DNA. One of these primers will have the same sequence as the natural DNA.

EXAMPLE III—HUMAN FIBROBLAST INTERFERON

Messenger RNA from human fibroblast cells is isolated and complementary DNA is made in accordance with the techniques previously described. The 3' hydroxyl ends of the complementary DNAs are then blocked by either one of the techniques described in Example I.

The first four amino acids of human fibroblast interferon are Met-Ser-Tyr-Asn. Accordingly, there are twelve possible primers of the possible bases as follows:

| Met | Ser | Tyr | Asn |
| --- | --- | --- | --- |
| ATG | TCT | TAT | AA |
| | TCC | TAC | |
| | TCG | | |
| | TCA | | |
| | AGT | | |
| | AGC | | |

These primers, individually or as a mixture, are used for synthesizing the second strand of DNA. One of these primers will have the same sequence as the natural RNA.

It may be seen, therefore, that the invention provides an improved method for synthesizing double-stranded DNA which inherently provides a very strong purification of the double-stranded DNA sequences. The method makes it possible to obtain specific double-stranded DNA using messenger RNA with high yields and with a relatively minimal number of steps. Extensive separation or purification procedures as are frequently required by prior art techniques, are not necessary.

Various modifications of the invention in addition to those shown and described herein will become apparent to those skilled in the art from the foregoing description and accompanying drawings. Such modifications are intended to fall within the scope of the appended claims.

What is claimed is:

1. A method for constructing double-stranded DNA having a strand which codes for a specific strand of messenger RNA, wherein single strands of a first DNA complementary to the specific strand of messenger RNA are provided, comprising blocking the free 3' hydroxy end of said first complementary DNA, providing at least one specific primer segment comprising a second DNA complementary to a preselected portion of the single strands of said first complementary DNA, said preselected portion of said first complementary DNA being in the region thereof which codes for the amino terminus end of the protein which the messenger RNA encodes and extending said specific primer segment with bases complementary to the single strands of said first DNA to form double-stranded DNA one strand of which codes for the specific strand of messenger RNA.

2. A method according to claim 1 wherein at least one specific primer segment has a nucleotide sequence coding for a plurality of amino acids in the region of the amino terminus end of the protein coded by the specific strand of messenger RNA.

3. A method according to claim 1 wherein the single strands of said first DNA are provided by extension from a nonspecific primer complementary to the 3' hydroxy terminus of messenger RNA strands in a population which comprising the specific strands, and wherein the specific primer segments are selected to anneal to those of the single strands of DNA which code for the specific strand of messenger RNA.

4. A method according to claim 2 wherein the single strands of said DNA complementary to messenger strands are formed using reverse transcriptase.

5. A method according to claim 1 wherein blocking is accomplished by treatment of the single strands of DNA with chain-terminating nucleoside triphosphates in the presence of a polymerase or deoxynucleotidyl terminal transferase.

6. A method for constructing double-stranded DNA coding for a specific protein, comprising, providing a mix of a plurality of different messenger RNA strands including specific messenger RNA strands coding for the specific protein, forming single strands of DNA complementary to the plurality of different messenger RNA strands in the mix using a non-specific 3' hydroxy terminus primer, separating the thus formed single strands of complementary DNA from the messenger RNA, providing primer segments of DNA complementary to a protein of those of the thus formed single strands of complementary DNA which code for the specific strand of messenger RNA, such primer segments preselected to anneal in the region of the amino terminus coding ends of the thus formed single strands of complementary DNA which codes for the specific strands of messenger RNA, blocking the free 3' hydroxy end of said single strands of DNA complementary to said plurality of different messenger RNA prior to annealing said primer segments thereto, annealing said primer segments to said blocked single strands of complementary DNA and extending the primer segments with bases complementary to the single strands of complementary DNA to form double-stranded DNA coding for the specific strand of messenger RNA.

7. A method according to claim 6 wherein the single strands of complementary DNA are formed using reverse transcriptase.

8. A method according to claim 7 wherein the free 3' hydroxy of the complementary DNA molecules in the single strands of DNA are blocked prior to annealing the primer segments of DNA thereto.

9. A method according to claim 8 wherein blocking is accomplished by treatment of the single strands of DNA with chain-terminating nucleoside triphosphates in the presence of a polymerase or deoxynucleotidyl terminal transferase.

10. A method for constructing double-stranded DNA coding for a specific strand of messenger RNA in a mix of a plurality of different messenger RNA strands, comprising, providing a plurality of nonspecific DNA primer segments complementary to the messenger RNA bases coding for the 3' hydroxyl terminus of the messenger RNA strands, annealing said first primer segments to the complementary portions of the messenger RNA strands, extending the first primer segments by reverse transcriptase to form single strands of DNA complementary to the RNA strands said single strands of DNA each having a hook at the amino terminus coding end thereof, separating messenger RNA, disabling said hooks from having a primer function in the presence of DNA polymerase, providing a plurality of second DNA primer segments complementary to a plurality of known DNA bases in the region of the 5' ends of those of said single strands of DNA complementary to the specific strand of messenger DNA, annealing said second DNA primer segments to the complementary portion of the single strands of DNA, and extending said second primer fragments to form double-stranded DNA coding for said specific messenger strands.

11. A method according to claim 10 wherein said hooks are disabled by blocking the free 3' hydroxy group thereof by treatment with chain-terminating nucleoside triphosphates in the presence of a polymerase or deoxynucleotidyl terminal transferase.

12. A method according to claim 10 wherein the specific primer segments are synthesized to code for a plurality of amino acids in the region of the amino terminus of the protein corresponding to the specific strand of messenger RNA.

* * * * *